US010626457B2

(12) United States Patent
Saxena et al.

(10) Patent No.: US 10,626,457 B2
(45) Date of Patent: Apr. 21, 2020

(54) ARRAYS OF OPTICAL DEVICES COMPRISING INTEGRATED BANDPASS FILTERS AND METHODS OF PRODUCTION

(71) Applicants: Pacific Biosciences of California, Inc., Menlo Park, CA (US); IMEC vzw, Leuven (BE)

(72) Inventors: Ravi Saxena, San Francisco, CA (US); Annette Grot, Cupertino, CA (US); Nicolaas Tack, Buggenhout (BE); Pilar Gonzalez, Bormujos (ES); Bert Du Bois, Blanden (BE); Simone Severi, Leuven (BE)

(73) Assignee: Pacific Biosciences of California, Inc., Menlo Park, CA (US)

( * ) Notice: Subject to any disclaimer, the term of this patent is extended or adjusted under 35 U.S.C. 154(b) by 303 days.

(21) Appl. No.: 15/337,711

(22) Filed: Oct. 28, 2016

(65) Prior Publication Data

US 2017/0145498 A1 May 25, 2017

Related U.S. Application Data

(60) Provisional application No. 62/247,684, filed on Oct. 28, 2015.

(51) Int. Cl.

| | | |
|---|---|---|
| *G01N 21/00* | (2006.01) | |
| *C12Q 1/6874* | (2018.01) | |
| *G02B 5/20* | (2006.01) | |
| *G02B 5/28* | (2006.01) | |
| *G02B 3/00* | (2006.01) | |
| *G02B 5/18* | (2006.01) | |
| *G02B 27/09* | (2006.01) | |
| *G01N 21/64* | (2006.01) | |

(52) U.S. Cl.
CPC ......... *C12Q 1/6874* (2013.01); *G01N 21/648* (2013.01); *G01N 21/6454* (2013.01); *G02B 3/0006* (2013.01); *G02B 5/1819* (2013.01); *G02B 5/201* (2013.01); *G02B 5/288* (2013.01); *G02B 27/0944* (2013.01); *G01N 2021/6419* (2013.01); *G01N 2021/6421* (2013.01); *G01N 2021/6463* (2013.01); *G01N 2021/6471* (2013.01)

(58) Field of Classification Search
CPC ............... G01N 21/78; G01N 21/6428; G01N 2021/7786
USPC .................................... 422/82.05, 82.08, 603
See application file for complete search history.

(56) References Cited

U.S. PATENT DOCUMENTS

| | | |
|---|---|---|
| 4,957,371 A | 9/1990 | Pellicori et al. |
| 5,144,498 A | 9/1992 | Vincent |
| 5,159,199 A | 10/1992 | Labaw |
| 5,410,431 A | 4/1995 | Southwell |
| 5,999,322 A | 12/1999 | Cushing |
| 6,011,652 A | 1/2000 | Cushing |
| 6,631,033 B1 | 10/2003 | Lewis |
| 6,917,726 B2 | 7/2005 | Levene et al. |
| 7,002,697 B2 | 2/2006 | Domash et al. |
| 7,170,050 B2 | 1/2007 | Turner et al. |
| 7,181,122 B1 | 2/2007 | Levene et al. |
| 7,250,591 B2 | 7/2007 | Mouli |
| 7,820,983 B2 | 10/2010 | Lundquist et al. |
| 7,901,870 B1 | 3/2011 | Wach |
| 7,907,800 B2 | 3/2011 | Foquet et al. |
| 8,071,416 B2 | 12/2011 | Liu et al. |
| 8,330,840 B2 | 12/2012 | Lenchenkov |
| 9,223,084 B2 | 12/2015 | Grot et al. |
| 9,372,308 B1 | 6/2016 | Saxena et al. |
| 9,606,068 B2 | 3/2017 | Grot et al. |
| 2002/0080493 A1 | 6/2002 | Tsai et al. |
| 2002/0131047 A1 | 9/2002 | Zarrabian et al. |
| 2003/0048985 A1 | 3/2003 | Hulse |
| 2003/0148542 A1 | 8/2003 | Pawlak et al. |
| 2004/0234417 A1* | 11/2004 | Schienle ............ G01N 21/6454 422/82.08 |
| 2006/0198025 A1 | 9/2006 | Chen |
| 2007/0134128 A1 | 6/2007 | Korlach |
| 2008/0042782 A1 | 2/2008 | Wang et al. |
| 2008/0176769 A1 | 7/2008 | Rank et al. |
| 2009/0208957 A1 | 8/2009 | Korlach et al. |
| 2010/0255488 A1 | 10/2010 | Kong et al. |
| 2011/0128423 A1 | 6/2011 | Lee et al. |
| 2011/0183409 A1 | 7/2011 | Newby et al. |

(Continued)

OTHER PUBLICATIONS

Modreanu et al. (1998) IEEE International Semiconductor Conference; CAS '98 Proceedings, 201-204; DOI: 10.1109/SMICND.1998. 732342.
Sedky et al. (2001) IEEE Transactions on Electron Devices, 48 377-385.
Morton et al. (2003) Society of Vacuum Coaters, 46th Annual Technical Conference Proceedings.
Hu et al. (2004) J. Crystal Growth 264:7.
Witvroux et al. (2004) Mat. Res. Soc. Symp. Proc. 782 A2.1.1-A2. 1.12.
Takeuchi et al. (2005) IEEE Transactions on Electron Devices, 52 2081-2086.

(Continued)

*Primary Examiner* — Natalia Levkovich
(74) *Attorney, Agent, or Firm* — VLP Law Group LLP

(57) ABSTRACT

Arrays of integrated optical devices and their methods for production are provided. The devices include an integrated bandpass filter layer that comprises at least two multi-cavity filter elements with different central bandpass wavelengths. The device arrays are useful in the analysis of highly multiplexed optical reactions in large numbers at high densities, including biochemical reactions, such as nucleic acid sequencing reactions. The devices provide for the efficient and reliable coupling of optical excitation energy from an optical source to the optical reactions. Optical signals emitted from the reactions can thus be measured with high sensitivity and discrimination. The device arrays are well suited for miniaturization and high throughput.

28 Claims, 9 Drawing Sheets

(56) References Cited

U.S. PATENT DOCUMENTS

| | | |
|---|---|---|
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0052506 A1 | 3/2012 | Yue et al. |
| 2012/0058469 A1 | 3/2012 | Shen |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1 | 4/2012 | Zhong et al. |
| 2012/0257047 A1 | 10/2012 | Biesemans et al. |
| 2012/0327248 A1 | 12/2012 | Tack et al. |
| 2013/0099112 A1 | 4/2013 | Haase et al. |
| 2013/0155515 A1 | 6/2013 | Song et al. |
| 2013/0240359 A1 | 9/2013 | Turner et al. |
| 2013/0338010 A1 | 12/2013 | Turner et al. |
| 2014/0175265 A1 | 6/2014 | Gonzalez et al. |
| 2014/0287964 A1 | 9/2014 | Lundquist et al. |
| 2015/0050659 A1 | 2/2015 | Sebo et al. |
| 2016/0061740 A1 | 3/2016 | Grot et al. |
| 2016/0154165 A1 | 6/2016 | Grot et al. |
| 2016/0237279 A1 | 8/2016 | Zheng et al. |

OTHER PUBLICATIONS

Wang et al. (2006) Appl. Phys. B 82:637.
Feb. 27, 2017 International Search Report and Written Opinion in PCT/US2016/059435.
Schott Interference Filters and Special Filters Catalog.
Deng et al. (2010) IEEE Symposium on Photonics and Optoelectronics (SOPO), Chengdu, China; DOI: 10.1109/SOPO.2010.5504008.

* cited by examiner

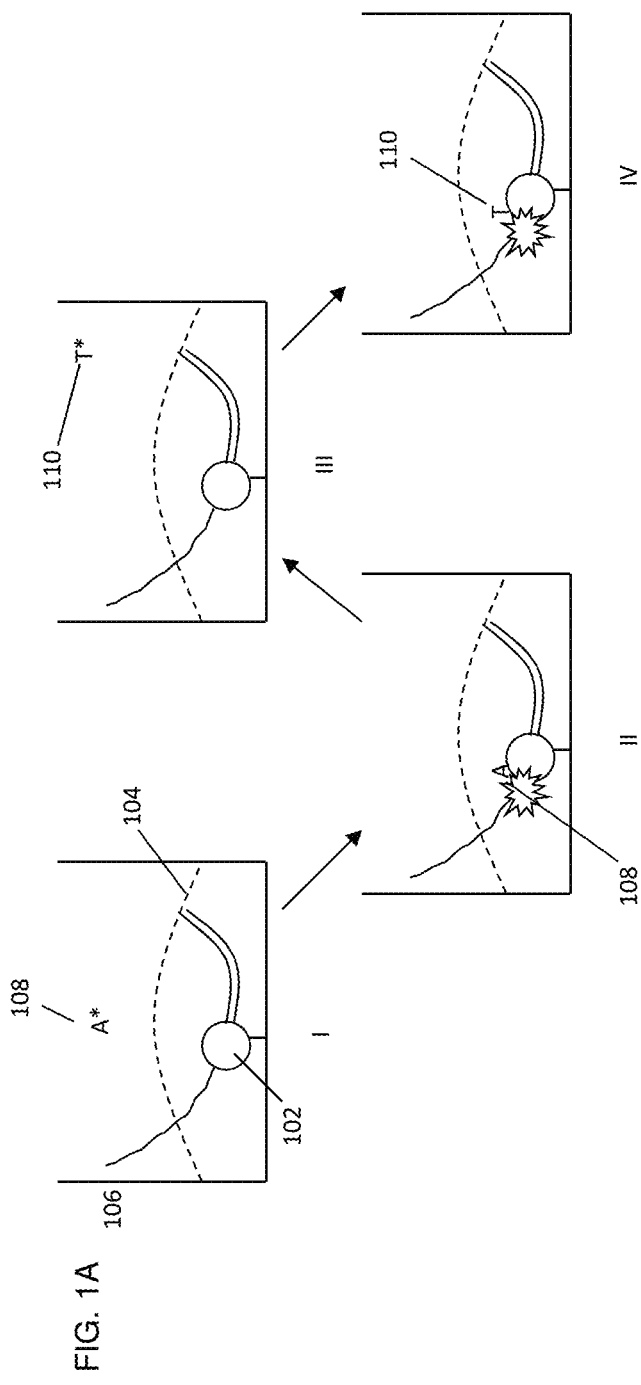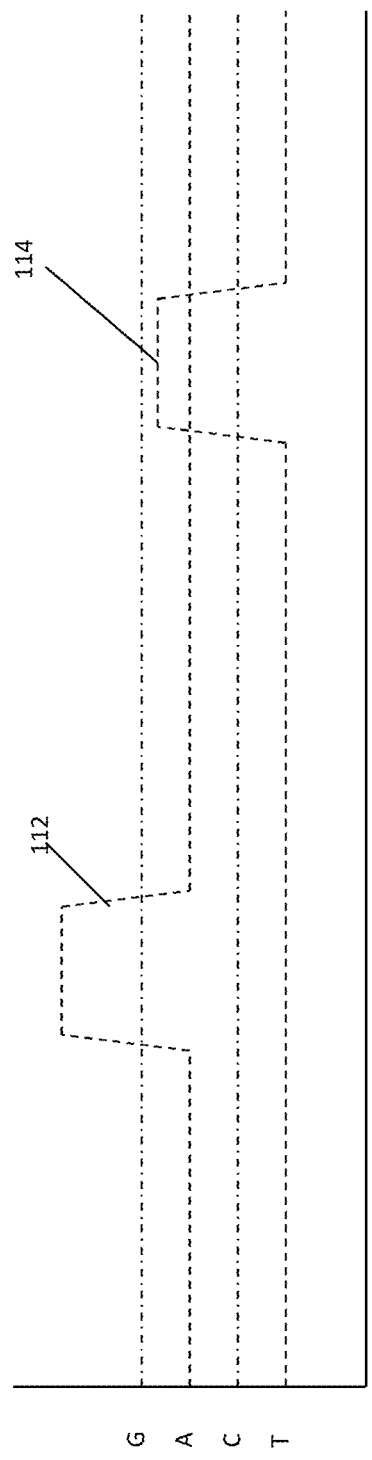
FIG. 1A
FIG. 1B

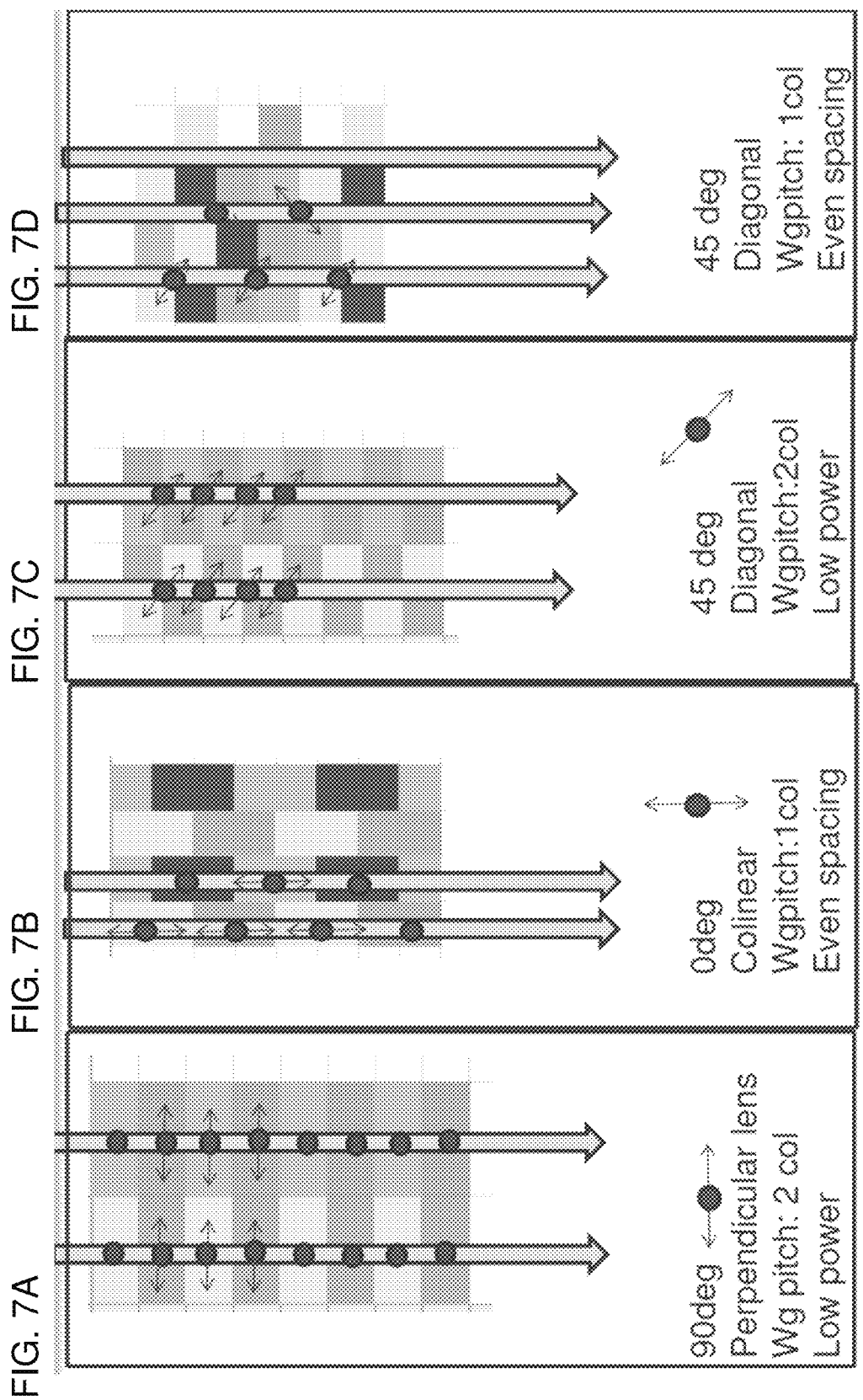

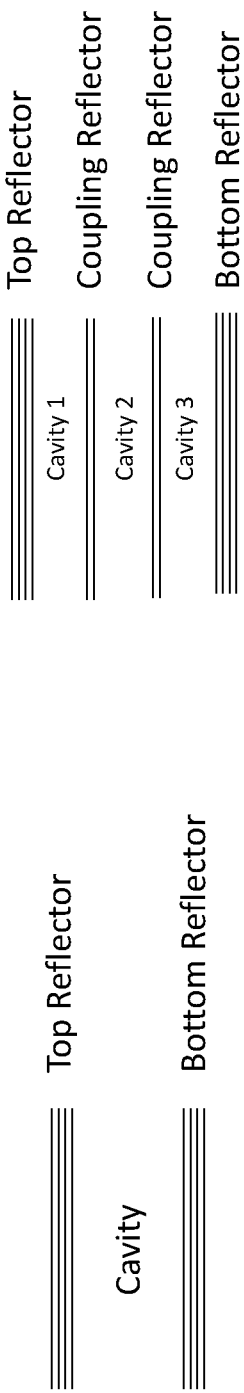
FIG. 8A
FIG. 8B
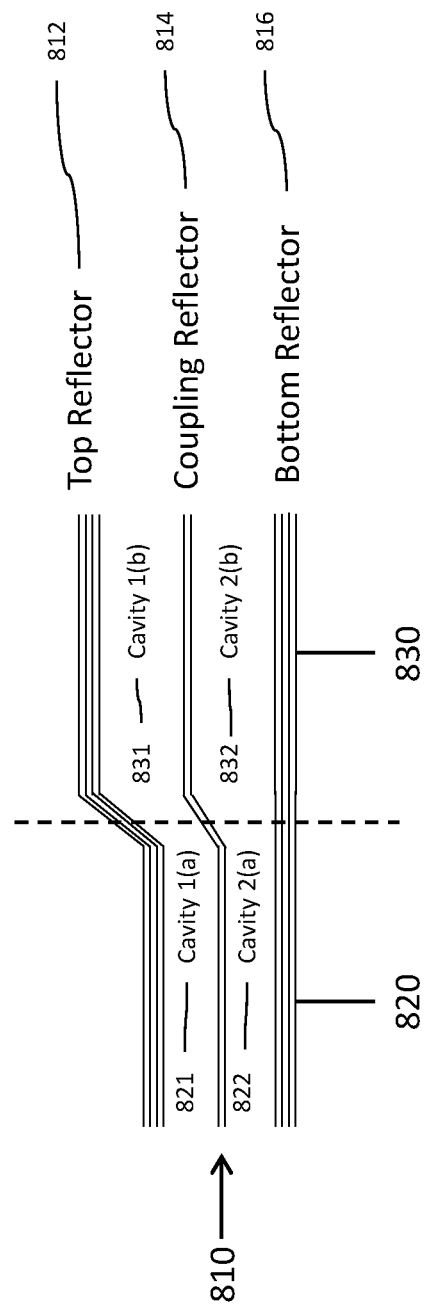
FIG. 8C

ARRAYS OF OPTICAL DEVICES COMPRISING INTEGRATED BANDPASS FILTERS AND METHODS OF PRODUCTION

CROSS-REFERENCE TO RELATED APPLICATIONS

This application claims the benefit of U.S. Provisional Application No. 62/247,684, filed on Oct. 28, 2015, the disclosure of which is incorporated herein by reference in its entirety.

BACKGROUND OF THE INVENTION

In analytical systems, the ability to increase the number of analyses being carried out at any given time by a given system has been a key component to increasing the utility and extending the lifespan of such systems. In particular, by increasing the multiplex factor of analyses with a given system, one can increase the overall throughput of the system, thereby increasing its usefulness while decreasing the costs associated with that use.

In optical analyses, increasing multiplex often poses increased difficulties, as it can require more complex optical systems, increased illumination or detection capabilities, and new reaction containment strategies. In some cases, systems seek to increase multiplex by many fold, and even orders of magnitude, which further implicate these considerations. Likewise, in certain cases, the analytical environment for which the systems are to be used is so highly sensitive that variations among different analyses in a given system may not be tolerable. These goals are often at odds with a brute force approach of simply making systems bigger and of higher power, as such steps often give rise to even greater consequences, e.g., in inter reaction cross-talk, decreased signal to noise ratios resulting from either or both of lower signal and higher noise, and the like. It would therefore be desirable to provide analytical systems that have substantially increased multiplex for their desired analysis, and particularly for use in highly sensitive reaction analyses, and in many cases, to do so while minimizing negative impacts of such increased multiplex.

At the same time, there is a continuing need to increase the performance of analytical systems and reduce the cost associated with manufacturing and using the system. In particular, there is a continuing need to increase the throughput of analytical systems. There is a continuing need to reduce the size and complexity of analytical systems. There is a continuing need for analytical systems that have flexible configurations and are easily scalable.

SUMMARY OF THE INVENTION

The instant invention addresses these and other problems by providing in one aspect an array of integrated analytical devices, each device comprising a nanoscale emission volume, a detector layer optically coupled to the nanoscale emission volume, wherein the detector layer comprises a first pixel and a second pixel, and a color filtration layer disposed between the nanoscale emission volume and the detector layer. In these devices, the color filtration layer comprises a first multi-cavity filter element and a second multi-cavity filter element, wherein the nanoscale emission volume is optically coupled through the first multi-cavity filter element to the first pixel and is optically coupled through the second multi-cavity filter element to the second pixel.

In some embodiments, the first and the second multi-cavity filter elements comprise alternating layers of a high refractive index material and a low refractive index material. In some embodiments, the first and the second multi-cavity filter elements each independently comprise a plurality of low refractive index cavity layers. In some embodiments, the first and the second multi-cavity filter elements each independently comprise a plurality of reflector layers bounding a plurality of low refractive index cavity layers.

In some embodiments, the arrays further comprise a lens element layer disposed between the nanoscale emission volume and the detector layer, and in some embodiments, the arrays further comprise an excitation source optically coupled to the nanoscale emission volume.

In some embodiments, the detector layer further comprises a third pixel, the color filtration layer further comprises a third multi-cavity filter element, and the nanoscale emission volume is optically coupled through the third multi-cavity filter element to the third pixel.

According to another aspect, the disclosure provides an array of integrated analytical devices comprising an array of nanoscale emission volumes and an array of first and second multi-cavity filter elements, each first and second multi-cavity filter element optically coupled to a nanoscale emission volume. In these arrays, each multi-cavity filter element comprises a bottom reflector layer comprising alternating layers of a low refractive index material and a high refractive index material, a first cavity layer disposed on the bottom reflector layer, wherein the first cavity layer comprises the low refractive index material, a first coupling reflector layer disposed on the first cavity layer, wherein the first coupling reflector layer comprises alternating layers of the low refractive index material and the high refractive index material, a second cavity layer disposed on the first coupling reflector layer, wherein the second cavity layer comprises the low refractive index material, and a top reflector layer disposed above the second cavity layer, wherein the top reflector layer comprises alternating layers of the low refractive index material and the high refractive index material. In these arrays, the first and second cavity layers of the first multi-cavity filter element have a first thickness and the first and second cavity layers of the second multi-cavity filter element have a second thickness.

In some embodiments, the arrays further comprise an array of detector elements, each detector element comprising a first pixel and a second pixel, wherein the multi-cavity filter elements are optically coupled to the detector elements. In some embodiments, the arrays further comprise an array of lens elements disposed between the array of nanoscale emission volumes and the array of detector elements. In some embodiments, the arrays further comprise an excitation source optically coupled to the nanoscale emission volumes.

According to yet another aspect, the disclosure provides methods for producing an array of integrated analytical devices comprising the steps of providing a substrate layer, depositing a bottom reflector layer on the substrate layer, wherein the bottom reflector layer comprises alternating layers of a low refractive index material and a high refractive index material, depositing a first cavity layer on the bottom reflector layer, wherein the first cavity layer comprises the low refractive index material, patterning and etching the first cavity layer to create a first arrangement of first cavity filter elements having a first thickness and second cavity filter elements having a second thickness, depositing a first coupling reflector layer on the first cavity layer, wherein the first coupling reflector layer comprises alternating layers of the low refractive index material and the high refractive index material, depositing a second cavity layer on the first coupling reflector layer, wherein the second cavity layer comprises the low refractive index material, patterning and etching the second cavity layer to create a second arrangement of first cavity filter elements having the first thickness and second cavity filter elements having the second thickness, and depositing a top reflector layer on the array, wherein the top reflector layer comprises alternating layers of the low refractive index material and the high refractive index material. In these methods, the first cavity filter elements of the first cavity layer are optically coupled to the first cavity filter elements of the second cavity layer, and the second cavity filter elements of the first cavity layer are optically coupled to the second cavity filter elements of the second cavity layer.

BRIEF DESCRIPTION OF THE DRAWINGS

FIGS. 1A-1B schematically illustrate an exemplary nucleic acid sequencing process that can be carried out using the disclosed arrays of integrated analytical devices.

FIGS. 7A-7D illustrate the layouts of integrated devices within exemplary arrays of the disclosure, showing the different arrangements of components within the devices.

FIG. 8A illustrates the structure of an exemplary single-cavity thin-film interference filter. FIG. 8B illustrates the structure of an exemplary multi-cavity thin-film interference filter. FIG. 8C illustrates the structure of the color filtration layer of an exemplary integrated analytical device of the instant disclosure, where the color filtration layer comprises two multi-cavity filter elements differing only in the thickness of the cavity layers.

DETAILED DESCRIPTION OF THE INVENTION

Integrated Analytical Devices

Figure 2:
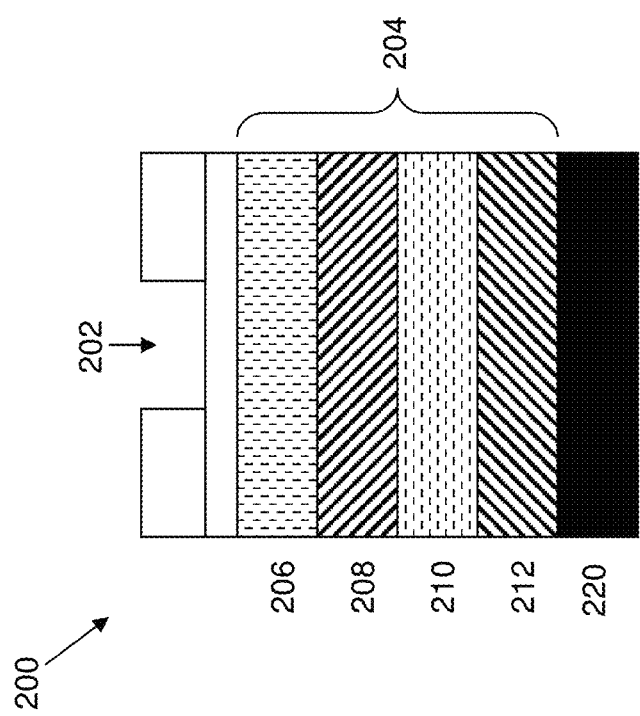
FIG. 2 provides a schematic block diagram of an integrated analytical device.

Multiplexed optical analytical systems are used in a wide variety of different applications. Such applications can include the analysis of single molecules, and can involve observing, for example, single biomolecules in real time as they carry out reactions. For ease of discussion, such multiplexed systems are discussed herein in terms of a preferred application: the analysis of nucleic acid sequence information, and particularly, single molecule nucleic acid sequence analysis. Although described in terms of a particular application, it should be appreciated that the applications for the devices and systems described herein are of broader application.

In the context of single molecule nucleic acid sequencing analyses, a single immobilized nucleic acid synthesis complex, comprising a polymerase enzyme, a template nucleic acid with nucleotide sequence of interest, and a primer sequence that is complementary to a portion of the template sequence, is observed to identify individual nucleotides as they are incorporated into the extended primer sequence. Incorporation is typically monitored by observing an optically detectable label on the nucleotide, prior to, during, or following its incorporation. In some cases, such single molecule analyses employ a "one base at a time approach", whereby a single type of labeled nucleotide is introduced to and contacted with the complex at a time. Upon incorporation, unincorporated nucleotides are washed away from the complex, and the labeled incorporated nucleotides are detected as a part of the immobilized complex.

In some instances, only a single type of nucleotide is added to detect incorporation. These methods then require a cycling through of the various different types of nucleotides (e.g., A, T, G and C) to be able to determine the sequence of the template. Because only a single type of nucleotide is contacted with the complex at any given time, any incorporation event is by definition, an incorporation of the contacted nucleotide. These methods, while somewhat effective, generally suffer from difficulties when the template sequence includes multiple repeated nucleotides, as multiple bases can be incorporated that are indistinguishable from a single incorporation event. In some cases, proposed solutions to this issue include adjusting the concentrations of nucleotides present to ensure that single incorporation events are kinetically favored.

In other cases, multiple types of nucleotides are added simultaneously, but the nucleotides are distinguishable by the presence on each type of nucleotide of a different optical label. Accordingly, such methods can use a single step to identify a given base in the sequence. In particular, all four nucleotides, each bearing a distinguishable label, is added to the immobilized complex. The complex is then interrogated to identify which type of base was incorporated, and as such, the next base in the template sequence.

In some cases, these methods only monitor the addition of one base at a time, and as such, they (and in some cases, the single nucleotide contact methods) require additional controls to avoid multiple bases being added in any given step, and thus being missed by the detection system. Typically, such methods employ terminator groups on the nucleotide that prevent further extension of the primer once one nucleotide has been incorporated. These terminator groups are typically removable, allowing the controlled re-extension after a detected incorporation event. Likewise, in order to avoid confounding labels from previously incorporated nucleotides, the labeling groups on these nucleotides are typically configured to be removable or otherwise inactivatable.

In another process, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase-mediated template dependent primer extension reaction is monitored as it occurs. In preferred aspects, the template/polymerase primer complex is provided, typically immobilized, within an optically confined region, such as a zero mode waveguide (ZMW), or proximal to the surface of a transparent substrate, optical waveguide, or the like (see e.g., U.S. Pat. Nos. 6,917,726, and 7,170,050 and U.S. Patent Application Publication No. 2007/0134128, the full disclosures of which are hereby incorporated by reference herein in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated. Although the analyte of interest in the devices disclosed herein is a template/polymerase primer complex that is incorporating fluorescently-labeled nucleotides, it should be understood that other analytes of interest, in particular fluorescent analytes of interest, can be monitored using the devices of the instant disclosure.

A schematic illustration of this sequencing process is shown in FIGS. 1A-1B. As shown in FIG. 1A, an immobilized complex 102 of a polymerase enzyme, a template nucleic acid, and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation. The extended illumination produces a signal associated with the retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

The above sequencing reaction can be incorporated into a device, typically an integrated analytical device, that provides for the simultaneous observation of multiple sequencing reactions, ideally in real time. While the components of each device and the configuration of the devices in the system can vary, each integrated analytical device typically comprises, at least in part, the general structure shown as a block diagram in FIG. 2. As shown, an integrated analytical device 200 typically includes a reaction cell 202, in which the analyte (i.e., the polymerase-template complex and associated fluorescent reactants) is disposed and from which the optical signals emanate. The analysis system further includes a detector element 220, which is disposed in optical communication with (also referred to herein as being "optically coupled to") the reaction cell 202. Optical communication between the reaction cell 202 and the detector element 220 is provided by an optical train 204 comprised of one or more optical elements generally designated 206, 208, 210, and 212 for efficiently directing the signal from the reaction cell 202 to the detector 220. These optical elements generally comprise any number of elements, such as lenses, filters, gratings, mirrors, prisms, refractive material, apertures, or the like, or various combinations of these, depending upon the specifics of the application. By integrating these elements into a single device architecture, the efficiency of the optical coupling between the reaction cell and the detector is improved. Examples of integrated analytical systems, including various approaches for illuminating the reaction cell and detecting optical signals emitted from the reaction cell, are described in U.S. Patent Application Publication Nos. 2012/0014837, 2012/0019828, 2012/0021525, and 2016/0061740, and in U.S. Pat. No. 9,372,308, which are each incorporated by reference herein in their entireties for all purposes.

As noted above, an analyte (e.g., a polymerase-template complex with associated fluorescent reactants) disposed within a reaction cell (e.g., element 202 in FIG. 2) or otherwise immobilized on the surface of the device, emits light that is transmitted to a detector element (e.g., element 220 in FIG. 2). For fluorescent analytes, the analyte is illuminated by an excitation light source, whereas for other analytes, such as chemilunimescent or other such analytes, an excitation light source may not be necessary. At least a portion of the reaction cell volume, the emission volume, is optically coupled to the detector element, so that light emitted from an analyte within this volume is measured by the detector element. In order to maximize the number of analytes measured simultaneously, the size of the instant analytical devices are reduced as much as possible, so that the emission volume within each device is a nanoscale emission volume. Ideally, the optical coupling between the nanoscale emission volume and the detector element is highly efficient, in order to maximize the sensitivity of the device and maximize the signal output. As described in further detail below, light emitted from the nanoscale emission volume can be further manipulated, for example by lens elements and/or color filtration layers, prior to reaching the detector element.

Conventional analytical systems typically measure multiple spectrally distinct signals or signal events and must therefore utilize complex optical systems to separate and distinctly detect those different signal events. The optical path of an integrated device can be simplified, however, by a reduction in the amount or number of spectrally distinguishable signals that are detected. Such a reduction is ideally effected, however, without reducing the number of distinct reaction events that can be detected. For example, in an analytical system that distinguishes four different reactions based upon four different detectable signal events, where a typical system would assign a different signal spectrum to each different reaction, and thereby detect and distinguish each signal event, in an alternative approach, four different signal events would be represented by fewer than four different signal spectra, and would, instead, rely, at least in part, on other non-spectral distinctions between the signal events.

For example, a sequencing operation that would conventionally employ four spectrally distinguishable signals, e.g., a "four-color" sequencing system, in order to identify and characterize the incorporation of each of the four different nucleotides, could, in the context of an alternative configuration, employ a one-color or two-color analysis, e.g., relying upon a signals having only one or two distinct or distinguished spectral signals. However, in such an alternative configuration, this reduction in reliance on signal spectral complexity does not come at the expense of the ability to distinguish signals from multiple, i.e., a larger number of different signal producing reaction events. In particular, instead of relying solely on signal spectrum to distinguish reaction events, such an alternative configuration can rely upon one or more signal characteristics other than emission spectrum, including, for example, signal intensity, excitation spectrum, or both, to distinguish signal events from each other.

In one particular alternative configuration, the optical paths in an integrated analytical device can thus be simplified by utilizing signal intensity as a distinguishing feature between two or more signal events. In its simplest iteration, and with reference to an exemplary sequencing process, two different types of nucleotides would bear fluorescent labels that each emit fluorescence under the same excitation illumination, i.e., having the same or substantially overlapping spectral band, and thus would provide benefits of being excited using a single excitation source. The resulting signals from each fluorescent label would have distinct signal intensities or amplitudes under that same illumination, and would therefore be distinguishable by their respective signal amplitudes. These two signals could have partially or entirely overlapping emission spectra, but separation of the signals based upon any difference in emission spectrum would be unnecessary.

Accordingly, for analytical systems using two or more signal events that differ in signal amplitude, the integrated analytical devices of such systems can readily benefit through the removal of some or all of those components that would normally be used to separate spectrally distinct signals, such as multiple excitation sources and their associated optical trains, as well as the color separation optics, e.g., filters and dichroics, for the signal events, which in many cases, requires at least partially separate optical trains and detectors for each spectrally distinct signal. As a result, the optical paths for these integrated analytical devices are greatly simplified, allowing placement of detector elements in closer proximity to reaction cells, and improving overall performance of the detection process for these devices.

Figure 3A:
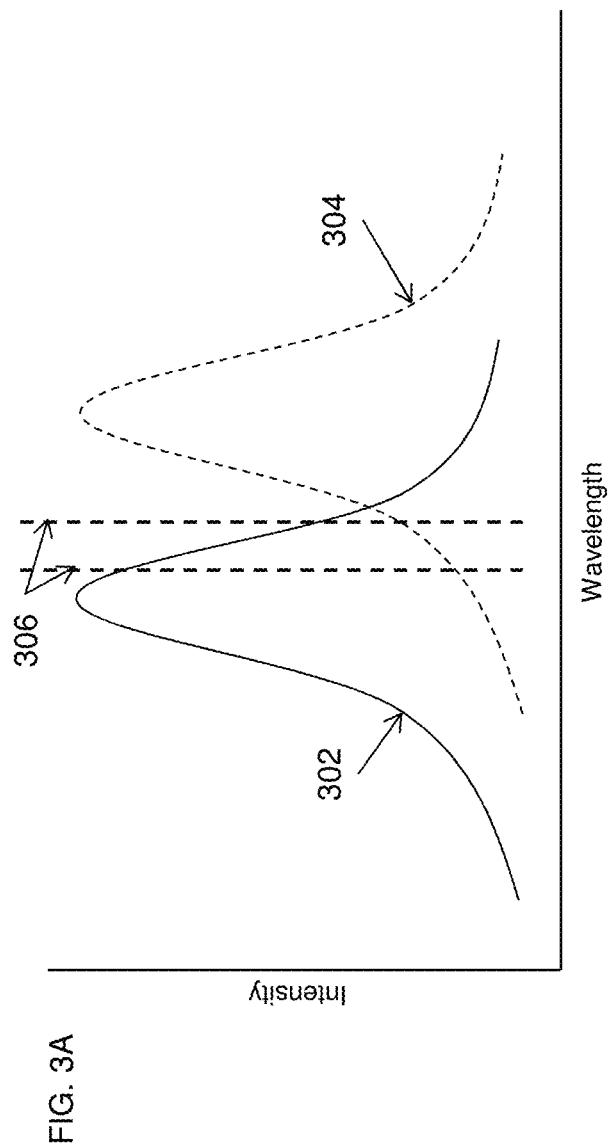
FIG. 3A provides a schematic of excitation spectra for two signal events and an indicated narrow band excitation illumination, while FIG. 3B schematically illustrates the resulting detected signal based upon the narrow band illumination of the two signal events.
Figure 3B:
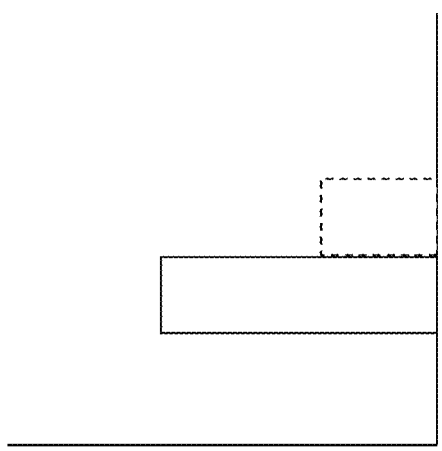

Provision of a signal-producing analyte that will produce different signal amplitudes under a particular excitation illumination profile can be accomplished in a number of ways. For example, different fluorescent labels can be used that present excitation spectral profiles that overlap but include different maxima. As such, excitation at a narrow wavelength will typically give rise to differing signal intensities for each fluorescent group. This is illustrated in FIG. 3A, which shows the excitation spectra of two different fluorescent label groups (solid and dashed lines 302 and 304, respectively). When subjected to excitation illumination at the wavelength range shown by vertical lines 306, each fluorescent label will emit a signal at the corresponding amplitude. The resulting signal intensities at a given excitation wavelength are then shown in the bar chart of FIG. 3B as solid lined and dashed lined bars, respectively. The difference in intensity of these two signal producing labels at the given excitation wavelength is readily used to distinguish the two signal events. As will be appreciated, such spectrally indistinct signals would not be easily distinguishable when occurring simultaneously, as they would result in an additive overlapping signal, unless, as discussed below, such spectrally indistinct signals result from spectrally distinct excitation wavelengths. As will be appreciated, this same approach can be used with more than two label groups, where the resulting emissions at a given excitation spectrum have distinguishable intensities or amplitudes.

Similarly, two different fluorescent labeling groups can have the same or substantially similar excitation spectra, but provide different and distinguishable signal emission intensities due to the quantum yield of those labeling groups.

Further, although described in terms of two distinct fluorescent dyes, it will be appreciated that each different labeling group can each include multiple labeling molecules. For example, each reactant can include an energy transfer dye pair that yields emissions of differing intensities upon excitation with a single illumination source. For example, a labeling group can include a donor fluorophore that is excited at a given excitation wavelength, and an acceptor fluorophore that is excited at the emission wavelength of the donor, resulting in energy transfer to the acceptor. By using different acceptors, whose excitation spectra overlap the emission spectrum of the donor to differing degrees, such an approach can produce overall labeling groups that emit at different signal amplitudes for a given excitation wavelength and level. Likewise, adjusting the energy transfer efficiency between the donor and acceptor will likewise result in differing signal intensities at a given excitation illumination.

Alternatively, different signal amplitudes can be provided by different multiples of signal producing label groups on a given reactant, e.g., putting a single label molecule on one reactant while putting 2, 3, 4, or more individual label molecules on a different reactant. The resulting emitted signal will be reflective of the number of labels present on a reactant and thus will be indicative of the identity of that reactant.

Exemplary compositions and methods relating to fluorescent reagents, such as nucleotide analogs, useful for the above purposes are described in, for example, U.S. Patent Application Publication Nos. 2012/0058473, 2012/0077189, 2012/0052506, 2012/0058469, 2012/0058482, 2010/0255488, 2009/0208957, 2015/0050659, and 2016/0237279, which are each incorporated by reference herein in their entireties for all purposes.

As described above, integrated analytical devices making use of such approaches see a reduction in complexity by elimination of spectral discrimination requirements, e.g., using signal amplitude or other non-spectral characteristics as a basis for signal discrimination. Integrated analytical devices that combine such non-spectral discrimination approaches with the more common spectral discrimination approaches can also provide advantages over more complex spectral discrimination systems. By shifting from a "four-color" discrimination system to a system that distinguishes signals based upon signal intensity and color, one can still reduce the complexity of the overall optical system relative to a conventional four-color separation scheme. For example, in an analytical operation that detects four discrete reaction events, e.g., in a nucleic acid sequencing analysis, two signal events can be provided within a given emission/detection spectrum, i.e., emitting signals within the same spectral window, and the other two events within a distinct emission/detection spectrum. Within each spectral window, the pair of signal events produce distinguishable signal intensities relative to each other.

For ease of discussion, this concept is described in terms of two groups of fluorescent signal events, where members of each group differ by fluorescent intensity, and the groups differ by virtue of their emission spectrum. As will be appreciated, the use of simplified optics systems, e.g., using two detection channels for two distinct emission spectra, does not require that the emission profiles of the two groups of signals do not overlap or that the emission spectra of members of each group perfectly overlap. Instead, in many preferred aspects, more complex signal profiles can be used where each different signal event possesses a unique emission spectrum, but in a way that each signal will present a signal profile within the two detection channels that is unique, based upon the signal intensity in each channel.

For use in the instant devices, each "emitter" in a sample should thus have a unique signal profile, as just described, in order to be properly identified. Samples containing a plurality of emitters can thus be readily distinguished using the instant devices. In some embodiments, the devices distinguish 4 to 18 emitters, 4 to 12 emitters, or even 4 to 8 emitters. In specific embodiments, the devices distinguish four emitters, for example the four different bases of the nucleic acid sequencing reaction.

Figure 4:
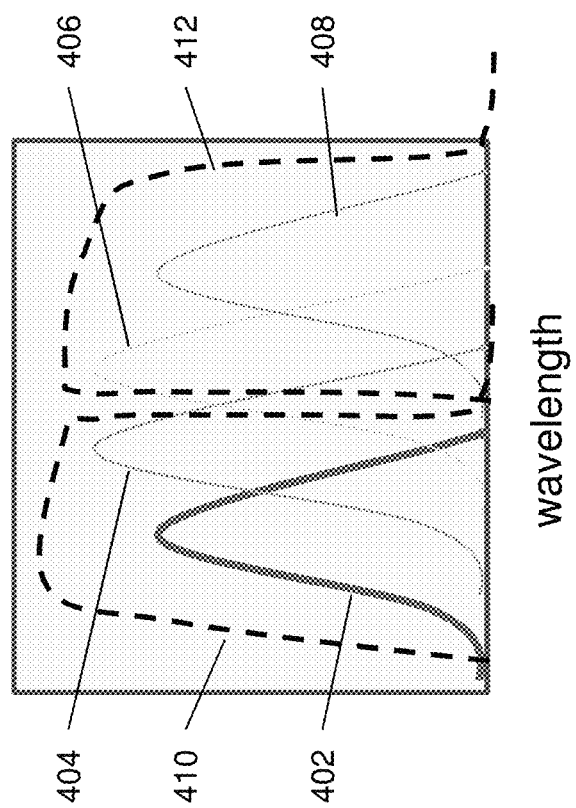
FIG. 4 schematically illustrates the signal profiles for each of four fluorescent labeling groups, overlain with each of two different color filter profiles.

FIG. 4 schematically illustrates the signal profiles for each of four fluorescent labeling groups, overlain with each of two different filter profiles. As shown, four label groups yield emission spectra 402, 404, 406, and 408, respectively. While the signals from these four groups partially overlap each other, they each have different maxima. When subjected to a two channel filter scheme, as shown by bandpass filter lines 410 and 412, the signal from each label will produce a unique signal profile between the two detection channels. In particular, signals are routed through an optical train that includes two paths that are filtered according to the spectral profile shown. For each signal, different levels of emitted light will pass through each path and be detected upon an associated detector. The amount of signal that passes through each filter path is dictated by the spectral characteristics of the signal. The color filter elements, as described in more detail below, are responsible for providing the desired bandpass characteristics for the device.

In the case of the above described mixed-mode schemes, detection systems can be provided that include at least two distinct detection channels, where each detection channel passes light within a spectrum that is different from each other channel. Such systems also include a reaction mixture within optical communication of the detection channels, where the reaction mixture produces at least three different optical signals that each produces a unique signal pattern within the two detection channels, as compared to the other optical signals.

In all cases, each signal-producing reactant is selected to provide a signal that is entirely distinct from each other signal in at least one of signal intensity and signal channel. As noted above, signal intensity in a given channel is dictated, in part, by the nature of the optical signal, e.g., its emission spectrum, as well as the filters through which that signal is passed, e.g., the portion of that spectrum that is allowed to reach the detector in a given channel. However, signal intensity can also be modulated by random variables, such as orientation of a label group when it is emitting signal, or other variables of the particular reaction. Accordingly, for a signal's intensity to be assured of being entirely different from the intensity of another signal within a given channel, in preferred aspects, this variation is accounted for.

Figure 5:
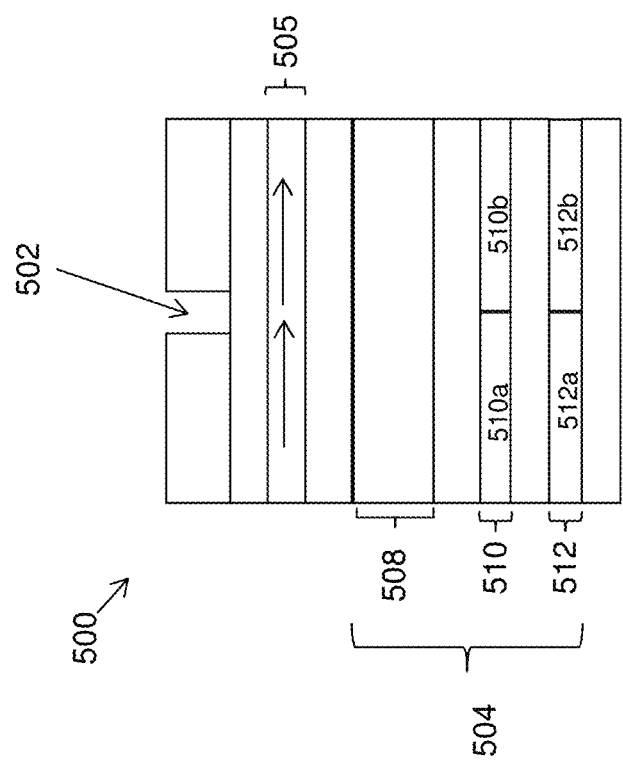
FIG. 5 schematically illustrates an integrated analytical device for detecting signals from a sequencing reaction, where a lens element spatially separates light emitted from a reaction cell, and directs the light through a color filtration layer and onto a detector layer.

With a reduced number of spectrally distinct signal events, the complexity of the optical paths for the integrated devices is also reduced. FIG. 5 illustrates a not-to-scale example device architecture for performing optical analyses, e.g., nucleic acid sequencing processes, that rely in part on non-spectral discrimination of differing signals in part on spectral distinction. As shown, an integrated analytical device 500 can include a reaction cell 502 that is defined upon the surface layer of the device. As shown in this drawing, the reaction cell comprises a nanowell disposed in the surface layer. Such nanowells can constitute depressions in a substrate surface or apertures disposed through additional substrate layers to an underlying transparent substrate, e.g., as used in zero mode waveguide (ZMW) arrays (see, e.g., U.S. Pat. Nos. 7,181,122 and 7,907,800). It should also be understood, however, that in some embodiments, the sample of interest can be confined in other ways, and that the nanoscale reaction cell in those embodiments can be omitted from the analytical devices. For example, if a target of interest is immobilized in a pattern on the surface of a device lacking separate reaction cells, binding events, or other events of interest, could be observed at those locations without the need for physical separation of the samples. Hybridization reactions, for example between immobilized nucleic acids and their complimentary sequences, or binding reactions, for example between antibodies and their ligands, where either member of the binding pair can be immobilized at a particular location on the surface of the device, could suitably be monitored using such an approach, as would be understood by those of ordinary skill in the art.

Excitation illumination is delivered to the reaction cell or to the immobilized target from an excitation light source (not shown) that can be separate from or also integrated into the substrate. As shown, an optical waveguide (or waveguide layer) 505 can be used to convey excitation light (shown by arrows in one direction, although light can be propagated in either direction or both directions, as desired) to the reaction cell 502 or otherwise immobilized target, where the evanescent field emanating from the waveguide 505 illuminates reactants within the illumination volume. Use of optical waveguides to illuminate reaction cells is described in e.g., U.S. Pat. Nos. 7,820,983 and 9,223,084, and U.S. Patent Application Publication Nos. 2012/0085894, 2014/0287964, and 2016/0154165, which are each incorporated by reference herein in their entireties for all purposes. The nanoscale reaction cell (also referred to herein as the "nanowell" or "ZMW") can act to enhance the emission of fluorescence downward into the device and limit the amount of light scattered upwards.

The emitted light, whether from a nanoscale reaction cell or from an immobilized target, is directed to the detector through an integrated optical train 504 comprising one or more optical elements. The optical train can include a lens element layer 508 to direct emitted light from an emission volume within the reaction cell to a detector layer 512 disposed beneath the reaction cell. The lens element layer in the integrated analytical devices of the instant disclosure may comprise, for example, a diffractive beam shaping element or other such component, that serves to separate at high efficiency the emitted light into at least two beams for passage through the color filtration layer 510. See, e.g., U.S. patent application Ser. No. 14/836,629, filed on Aug. 26, 2015, the disclosure of which is incorporated by reference herein for all purposes. The diffractive beam shaping element or other lens element can, for example, separate the emitted light into two, three, four, or even more at least partially separated beams directed onto the detector layer. Depending on the configuration of the diffractive beam shaping element or other lens element, the split beams can be organized in a linear fashion, or they can be arranged in an array, for example in a 2×2 beam array or the like. Such arrangements will typically be dictated by the configuration of the sensing regions of the detector layer.

The detector layer typically comprises one, or preferably multiple, sensing regions 512a-b, e.g., pixels in an array detector, for example a CMOS detector, that are optically coupled through the diffractive beam shaping element to an emission volume within a given analytical device. Although illustrated as a linear arrangement of pixels 512a-b, it will be appreciated that such pixels can be arranged in a grid, n×n square, n×m rectangle, annular array, or any other convenient orientation. Exemplary arrangements are described in more detail below and in FIG. 7.

It should be understood in the context of the disclosure that the optical coupling of two components in a device is not intended to imply a directionality to the coupling. In other words, since the transmission of optical energy through an optical device is fully reversible, the optical coupling of a first component to a second component should be considered equivalent to the optical coupling of the second component to the first component.

Emitted signals from an emission volume within reaction cell 502 of FIG. 5 that impinge on the pixels of the detector layer are detected and recorded by a computer or other processor associated with the analytical device. As noted above, and as will be described in further detail below, a color filtration layer 510 is preferably disposed between the detector layer and the nanoscale emission volume, to permit different spectrally distinct signals to travel to different associated sensing regions (i.e., pixels) 512a and 512b in the detector layer 512. For example, the filter element 510a of filtration layer 510 allows only signals having a distinct first emission spectrum to reach its associated sensing region 512a, while filter element 510b of filtration layer 510 allows only signals having a distinct second emission spectrum to reach its associated sensing region 512b. As described below, the filter elements of the color filtration layer are preferably multi-cavity filter elements, in particular, multi-cavity thin-film interference filter elements.

In the context of a sequencing system exploiting such a configuration, incorporation of two of the four nucleotides would produce signals that would be passed through filter element 510a to sensing region 512a, and blocked by filter element 510b. As between these two signals, one signal would have a signal intensity higher than the other, such that the sensing region 512a in detector layer 512 would be able to produce signal responses indicative of such differing signal intensities. Likewise, incorporation of the other two of the four nucleotides would produce signals that would be passed through filter element 510b to sensing region 512b, and blocked by filter element 510a. As between these two signals, one signal would have a signal intensity higher than the other, such that the sensing region 512b in detector layer 512 would be able to produce signal responses indicative of such differing signal intensities.

The detector layer is operably coupled to an appropriate circuitry, typically integrated into the substrate, for providing a signal response to a processor that is optionally included integrated within the same device structure or is separate from but electronically coupled to the detector layer and associated circuitry. Examples of types of circuitry are described in U.S. Patent Application Publication No. 2012/0019828.

As will be appreciated from the foregoing disclosure and FIG. 5, the integrated analytical devices described herein do not require the more complicated optical paths that are necessary in systems utilizing conventional four-color optics, obviating in some cases the need for excessive signal separation optics, dichroics, prisms, or filter layers. In particular, although shown with lens element layer 508, in optional aspects, the lens element layer could be eliminated or could be replaced with an alternative optical component, for example a filtration layer that blocks stray light from the excitation source, e.g., a laser rejection filter layer (see below), rather than distinguishing different emission signals from the reaction cell. Even including the lens element layer 508 results in simplified and/or more efficient optics as compared to conventional four-color systems, which require more complicated optical trains, thus blocking signal from reaching one or more of the sensing region subsets at any given emission wavelength, resulting in the detection of far fewer photons from each signal event. The optics configuration shown in FIG. 5, on the other hand, only blocks a smaller portion of the overall signal light from reaching the detector. For comparison, conventional systems would require separation and differential direction of all four different signal types, resulting in the inclusion of additional optical elements, e.g., prisms or gratings, to achieve spectral separation. Examples of nanoscale integrated analytical devices that include spectral diversion elements (i.e., optical elements that spatially separate light based on color) are provided in U.S. Patent Application Publication No. 2012/0021525.

Figure 6:
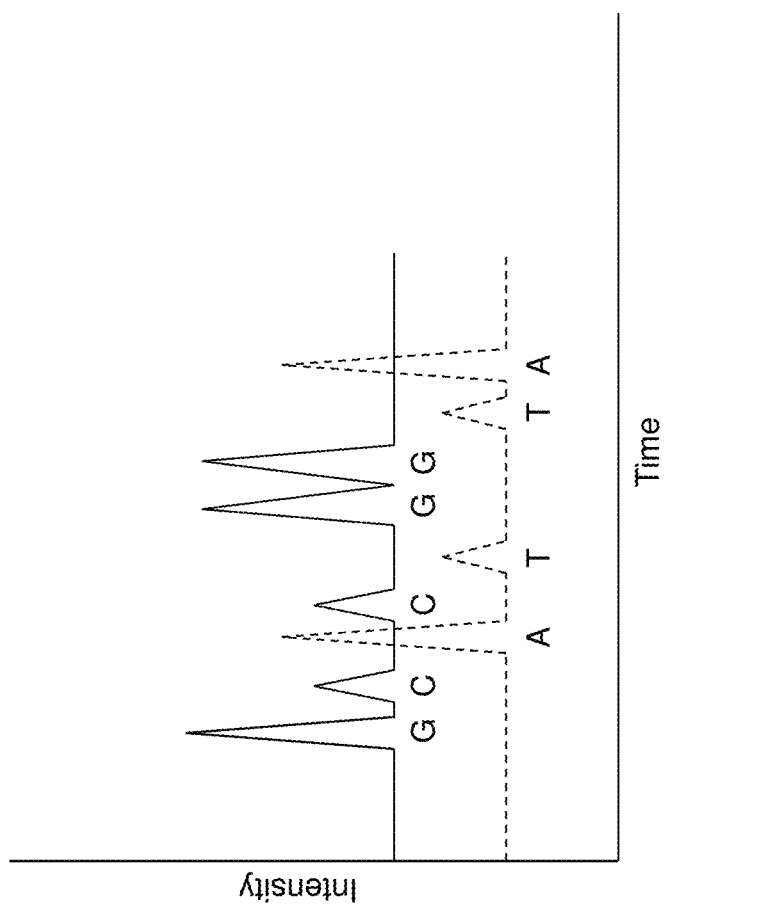
FIG. 6 schematically illustrates signal traces for a two-color, two-amplitude sequence-by-synthesis reaction.

FIG. 6 shows a schematic exemplar signal output for a real time sequencing operation using a two color/two amplitude signal set from an integrated system of the invention where one trace (dashed) denotes signals associated with incorporation of A (high intensity signal) and T (lower intensity signal) bases, while the other signal trace (solid line), denotes the signals of a different emission spectrum, associated with G (high) and C (low) bases. The timing of incorporation and the identity of the base incorporated, as derived from the color channel and intensity of the signal, are then used to interpret the base sequence.

FIGS. 7A-7D illustrate exemplary device layouts usefully employed in the arrays of the instant disclosure. In each case, the arrays are viewed from above, with dark circles representing the ZMWs/nanowells. As shown, the ZMWs/nanowells are positioned directly above waveguides, which are identified as broad arrows. In the case of the arrays shown in FIGS. 7A and 7C, the "pitch" of the waveguide is 2 columns (i.e., the waveguides are separated by the width of two columns of sensing regions/pixels), whereas for the arrays of FIGS. 7B and 7D, the pitch of the waveguide is 1 column (i.e., the waveguides are separated by the width of one column of sensing regions/pixels). The spatial separation of emitted light effected by diffractive beam shaping elements or other lens elements in each of the arrays is indicated by the two thin arrows associated with some of the ZMW/nanowells. For example, in the devices of FIG. 7A, the lens elements direct emitted light onto the two sensing regions that are aligned perpendicularly (i.e., at) 90° to the waveguide. In the devices of FIG. 7B, the lens elements direct emitted light onto the two sensing regions that are collinear (i.e., at 0°) with the waveguide. For the devices of FIGS. 7C and 7D, the lens elements direct emitted light onto the two sensing regions that are diagonal (i.e., at 45°) relative to the waveguide. As is apparent from the drawings, the devices of FIGS. 7C and 7D differ with respect to the pitch of the respective waveguides.

The arrays of integrated analytical devices shown in FIG. 7 are readily manufactured using standard microchip fabrication techniques and processes, as will be described in further detail below. For example, lithographic patterning and etching steps can be used to create the desired arrangements of optical components within each device of the array, for example the color filtration elements, the lens elements, the waveguides, the ZMWs/nanowells, and so forth. Multiple microfabrication steps may be necessary in some cases to generate some of the optical components, as would be understood by those of ordinary skill in the art.

Color Filter Elements

As described above, the integrated analytical devices of the instant disclosure include a color filtration layer, comprising a plurality of color filter elements, each of which is designed to transmit certain wavelengths of light, while significantly decreasing or blocking other wavelengths of light. In particular, it is desirable to transmit as much signal-related light as possible to the appropriate region of the detector, and to block all, or at least most, noise-related light. Furthermore, since the lens elements and other optical components of the instant devices are typically designed to transmit all wavelengths of light emitted from an analyte, it is typically desirable to employ color filter elements between the lens elements and the different sensing regions/pixels of the detector layer in order to distinguish different emitters in the analyte.

The integrated analytical devices of the instant disclosure therefore include a color filtration layer disposed between the nanoscale emission volume and the detector layer. A different color filter element within the color filtration layer is typically used for each of the spatially-separated beams transmitted to the detector. The spatially-separated light typically passes through the color filtration layer before being detected by the corresponding sensing region in the detector layer. Accordingly, the color filtration layer comprises a plurality of color filter elements, each color filter element specific to pass a range of light wavelengths. In specific embodiments, the color filtration layer comprises 2, 3, 4, 5, 6, or even more color filter elements. In more specific embodiments, the color filtration layer comprises 2 color filter elements, sensing regions, and separated beams, for example as shown in the block device schematized in FIG. 5 and in the device arrays illustrated graphically in FIGS. 7A-7D.

As just mentioned, the color filter elements are designed to transmit certain wavelengths of light while blocking other wavelengths of light. Suitable materials for use in the color filter elements of the instant devices include, for example, dielectric interference stacks, polymer-like resists, doped PECVD oxides, organo-silicone with absorbing dyes, and the like.

In preferred embodiments, the color filter elements of the instant devices are thin-film interference filters and in particular are multi-cavity thin-film interference filters. Thin-film interference filters can have very sharp transmission slopes, particularly when compared to absorption filters, so that the filters display steep optical cut-on and cut-off transition boundaries. Typical narrow bandpass, thin-film dielectric filters contain quarter-wave optical thickness "reflector" or "mirror" layers and half-wave optical thickness or multiple half-wave optical thickness "cavity" or "spacer" layers. See, e.g., Macleod (2001) *Thin-Film Optical Filters*, 3rd Ed. Chap. 7, Institute of Physics Publishing, Bristol and Philadelphia. For a single-cavity bandpass filter, the transmittance profile displays a triangular shape with high transmission at the center frequency of the cavity, and the filters consist of reflector structures on either side of a single cavity layer. See, e.g., Morton (2003) *Design of Multi-Band Square Band Pass Filters*, 46$^{th}$ Annual Technical Conference Proceedings, Society of Vacuum Coaters, 505/856-7188, Moorestown, N.J. FIG. 8A shows schematically a not-to-scale single-cavity thin-film interference filter element, where the cavity is a half-wave layer of transparent dielectric material, and the top and bottom reflectors are stacks of quarter-wave layers.

It should be understood that the thicknesses disclosed herein are, in some cases, physical thicknesses, but in other cases are understood to be relative to a wavelength of interest in the optical spectrum. For example, as just mentioned, some layers in the thin-film stacks use quarter-wave or half-wave optical thicknesses, where the optical thickness corresponds to an optical path length (physical thickness multiplied by the refractive index of the particular layer). It should also be understood that physical thicknesses and optical thicknesses are not absolute but can be, for example, within 5%, 10%, 15%, 20%, or even more, of the recited value. Where the same layer, for example a reflector layer, is shared by two filter elements designed to transmit two different wavelength ranges, or overlapping wavelength ranges, it may be desirable for the quarter-wave optical thickness of those layers to be based on, for example, an average of the two center frequencies of interest and thus to transmit an overlapping wavelength range.

Physical thicknesses of the individual layers of material in the thin-film stacks of the instant color filter elements can range from 5 nm to 5000 nm. Preferred physical thicknesses can range from 10 nm to 1000 nm. More preferred physical thicknesses for the individual layers in the reflector stacks can range from 10 nm to 200 nm and more specifically from 20 nm to 100 nm. More preferred physical thicknesses for the cavity layers can range from 40 nm to 400 nm and more specifically from 150 nm to 350 nm.

The bandwidth of a single- or multi-cavity filter depends on the relative refractive indices ("n") of the materials used to construct the reflector layers, the composition of the cavity layer, and the number of layers and/or periods of the reflectors. In general, it is preferable that the materials used to construct the reflector layers have as large a difference in refractive index as possible for a targeted specific wavelength range, and also that the optical absorption loss for the two materials be low.

Preferred values of refractive index for the high refractive index materials range, for example, from 2.5 to 5, more preferably from 2.5 to 3.5, and even more preferably from 2.5 to 3.0. Preferred values of refractive index for the low refractive index materials range, for example, from 1 to 1.8, more preferably from 1.2 to 1.7, and even more preferably from 1.4 to 1.6. It should be understood that because the refractive index of a material varies with the wavelength of light being transmitted through the material, a given refractive index typically corresponds to the refractive index of the material at the wavelength of interest.

The level of transparency of the materials used in the interference stacks, which is an indication of the optical absorption loss for the materials, is defined by the extinction coefficient ("k") of the materials. It is preferred that the materials be chosen to have a relatively high extinction coefficient (and thus low transmittance) at the wavelength of the excitation source (e.g., the laser or other optical input) and that the material is thus able to help block background input signals from reaching the detector. At the same time, it is preferred that the materials be chosen to have a relatively low extinction coefficient (and thus high transmittance) at the wavelength of emission of the analyte of interest, thus maximizing the amount of signal passing through the filter to the detector. Preferred values of the extinction coefficient for the materials in the thin-film stacks range, for example, from 0 to 0.2, and more preferably from 0 to 0.1, at the wavelength of emission of the analyte of interest.

Suitable high refractive index and low refractive index materials for use in the instant thin-film stacks can include various semiconductor materials, dielectric materials, and metals. For example, suitable materials can include, without limitation, C, Si, Ge, SiGe, various Group III-V compounds (e.g., $In_xGa_yAl_{1-x-y}As_zP_mSb_{1-z-m}$, where x, y, m, and z are all between 0 and 1), InGaAsNSb, various Group II-VI compounds (e.g., ZnCdSeS in various combinations). Exemplary metals can include Au, Ag, Al, and so forth. Exemplary dielectric materials can include BN, ZnOx, HfO, and so forth. Other useful combinations of materials can include, for example, Si/TiO$_2$, Si/air, GaAs/AlOx, ZnSe/CaF$_2$, and the like. Organic polymers can also be used for either or both of the high refractive index and low refractive index materials.

Preferred materials for use in the low refractive index layers of the instant color filtration layers are materials comprising a silicon oxide, in particular thin-film silicon dioxide materials. Preferred materials for use in the high refractive index layers of the instant color filtration layers are materials comprising silicon, for example the thin-film silicon materials disclosed in Modreanu et al. (1998) *IEEE Semiconductor Conference Proceedings*, vol. 1, DOI: 10.1109/SMICND.1998.732342; Deng et al. (2010) *IEEE Symposium on Photonics and Optoelectronic (SOPO)*, DOI: 10.1109/SOPO.2010.5504008; or Hu et al. (2004) *J. Crystal Growth* 264:7. Each of these references is incorporated by reference herein in its entirety for all purposes.

An additional consideration in the manufacture of the instant integrated devices can be the processing temperature for the low refractive index and high refractive index materials. Where the device arrays of the instant disclosure are fabricated on the surface of a CMOS sensor, or other temperature-sensitive surface, the materials used in the thin-film stacks are preferably chosen from materials that can be fabricated at temperatures that do not damage the CMOS sensor or other temperature-sensitive substrate.

The allowed thermal budget for the MEMS fabrication can accordingly depend on the CMOS technology considered. For example, the thermal budget limits for 0.35 µm standard CMOS wafers with aluminum-based interconnects were experimentally investigated by Sedky et al. (2001) *IEEE Trans. Electron Devices* 48:377-385 through annealing tests. As demonstrated there, the increase in the sheet resistance of the Al interconnects (possibly caused by the reaction of Al with Ti to form TiAl$_3$), rather than transistor performance, was the limiting factor. A similar study by Takeuchi et al. (2005) *IEEE Trans. Electron Devices* 52:2081-2086, showed that, for 0.25 µm standard CMOS wafers with aluminum-based interconnects, the thermal budget is mostly limited by an increase in the tungsten-filled intermetal vias. With a failure criterion of 10% increase, the maximum allowed post-processing thermal budget is 2 h at 450° C. or 30 min at 475° C. For more advanced CMOS technologies, where copper-based interconnects and low-permittivity dielectrics are employed as insulating intermetallic layers, the thermal constraints can be even more severe, for example as discussed by Witvrouw et al. (2004) *Materials Research Society Symp. Proc.* 782:A2.1.1. High index materials, such as polycrystalline silicon and gallium phosphate, while displaying suitable optical properties for use in thin-film filter stacks, typically require high processing temperatures and are therefore generally less suitable where a temperature-sensitive substrate is used in fabricating the devices. A high index material, such as the thin-film silicon materials described above, is better suited for lower-temperature fabrication, particularly when used in combination with a thin-film silicon dioxide material as the low refractive index material.

Thin-film interference filters typically contain many layers, stacked one on top of another. A further consideration in the manufacture of the instant integrated devices is therefore the risk of delamination of the filter stacks. This delamination might be due to mismatch between the residual stresses in the layers or might be due to the stresses generated in the layers due to the thermal budget of the deposition of subsequent layers in the stack. Furthermore, outgas sing of the underlying layers can result in bubble formation which can result in adhesion problems and delamination. These problems may be aggravated during the post-processing of the filters on top of the CMOS sensors, due to the extra stress coming from the CMOS layers. Excessive stress can also result in an excessive bow of the wafers. This excessive wafer bow can prevent a proper holding of the wafer by the vacuum chuck of the required processing tool, impeding further processing. These problems can be solved in different ways, for example by selecting filter materials with low residual stress and/or tuning the stress by varying the film deposition conditions, by introducing annealing steps in different parts of the flow to outgas the layers, by depositing a stress compensation layer on the backside of the wafer, or by other suitable methods.

By fabricating the optical filters using solely techniques and tools derived from standard IC (integrated circuit) manufacturing, an optimal quality of the thin films can be ensured. However, these IC-processing tools typically function at a restrictive contamination level. Accordingly, certain materials (e.g. Au, Ag) are preferably not integrated into the filter flow, since they can contaminate the tools used in the standard IC processing flow. Contamination of the IC tools can in turn negatively affect the yield of future devices processed in those tools because of diffusion of the contaminant material into the device layers. Therefore, even though the use of standard IC tools means that the filters can benefit from improved performance and yield, it also poses a restriction in the choice of materials. The materials chosen for the instant thin-film stacks are therefore preferably chosen to avoid contamination of the IC-processing tools.

Multi-cavity filters have additional partial reflector layers, also known as "coupling reflectors", and cavity layers within their structures. For example, FIG. 8B shows a not-to-scale schematic representation of a three-cavity band-pass filter with two coupling reflectors. A single-cavity filter can be described as having the structure $[HL]^x[LH]^x$, where H is a high-index material (e.g., TiO$_2$, a thin-film silicon material, or the like), L is a low-index material (e.g., SiO$_2$), and each x is independently the number of layers of [HL] or [LH] pairs (e.g., 4). By comparison, a multi-cavity filter can have the structure $[HL]^x[LH]^x[L][HL]^x[LH]^x$ or $[HL]^x[LH]^x[L]$ $[HL]^x[LH]^x[L][HL]^x[LH]^x$, where the $[HL]^x$ and $[LH]^x$ structures represent the reflector layers, with each x being independently the number of layers of [HL] or [LH] pairs. In all cases, the thicknesses of the low index cavity layers, which can also be multiples of a particular half-wave optical thickness, determine the central frequency of the filter, as is understood in the art.

Multi-cavity filters advantageously result in squared-off or rectangular-shaped pass regions, compared to single-cavity interference filters. See, e.g., Morton (2003) *Design of Multi-Band Square Band Pass Filters, 46$^{th}$ Annual Technical Conference Proceedings*, Society of Vacuum Coaters, 505/856-7188, Moorestown, N.J. See also, U.S. Pat. No. 6,011,652 and U.S. Patent Application Publication No. 2013/0155515 A1. Specifically, the pass region becomes more rectangular as the number of cavities increases. Increasing the multiplicity of low-index layers within a cavity results in a narrower bandpass. Mixing of thicknesses of cavity layers within a multi-cavity filter can also affect the width and the shape of the bandpass, as would be understood by those of ordinary skill in the art. As noted in U.S. Patent Application Publication No. 2013/0155515 A1, however, fabrication of multi-cavity filters can result in variability in the optical properties of the filters.

The multi-cavity filters of the instant analytical devices provide certain advantages over other types of color filters typically used in such devices, including single-cavity filters. In particular, as just mentioned, the shape of the pass region of a multi-cavity filter is more square and thus has much sharper edges than those of a single-cavity filter. A squared-off bandpass can be advantageous in the instant devices, where two or more closely-spaced emission colors from an analyte need to be distinguished with high reliability and sensitivity. Such filters thus minimize cross-talk between adjacent sensing regions/pixels within the detector layer. Multi-cavity filters also allow for wider transmission range as compared to their single-cavity counterparts. With proper design these multi-cavity filters can also be more robust to process variations.

In addition, multi-cavity thin-film interference filters can be more efficiently manufactured than other types of color filters using low-cost, high-yield microchip fabrication techniques, for example using standard deposition, patterning, and etching techniques. Such techniques are described in detail in U.S. patent application Ser. No. 13/920,037, filed on Jun. 17, 2013, and in U.S. Patent Application Publication No. 2012/0327248 A1, the disclosures of which are each incorporated by reference herein in their entireties for all purposes. In particular, the different multi-cavity filter elements of the instant devices can be built up on a substrate simultaneously, thus greatly simplifying the fabrication. This is possible because the materials used in each of the different color filtration elements can be the same, and the different elements can even use the same stack structure for the bottom and top reflector layers and for each of the intermediate coupling reflector layers. The different filter elements preferably vary only in the thicknesses of the low-index cavity layers, which are chosen to provide maximum passage of signal at the particular wavelengths emitted by the analytes of interest. FIG. 8C shows a not-to-scale schematic representation of a color filtration layer 810 with two multi-cavity filter elements (a) and (b) 820 and 830. As shown, both elements have the same reflector layers (top reflector layer 812, coupling reflector layer 814, and bottom reflector layer 816). The filter elements differ only in the thicknesses of the two cavity layers (cavity layer 1(a) 821 and cavity layer 2(a) 822 compared to cavity layer 1(b) 831 and cavity layer 2(b) 832), which are half-wave optical thicknesses or multiples thereof, and which are designed and optimized to pass light of two different desired ranges of wavelength.

The filter elements of the instant disclosure are generally designed to transmit light in the visible and infrared regions of the electromagnetic spectrum. The filter elements preferably transmit visible light, as most DNA sequencing reagents are designed to fluoresce in this region of the spectrum. In some embodiments, the filter elements transmit light having a wavelength range from 550 nm to 750 nm. In more specific embodiments, the filter elements transmit light having a wavelength range from 580 nm to 680 nm. In even more specific embodiments, the filter elements transmit light at 600 nm and 660 nm.

As a result of the above-described designs, the manufacturing process for the color filtration layer of the instant devices can also be greatly simplified compared to the processes required for devices having different materials in the different filter elements or for devices that need to distinguish larger numbers of colors. For example, the color filtration layer can be built up by the deposition of multiple layers of the high index and low index materials to generate a first reflector layer, represented by $[HL]^x$. As mentioned above, the first reflector layer is preferably the same across all color filter elements within a given device, where the quarter-wave optical thickness is chosen to accommodate the entire range of wavelengths emitted by the analytes of interest. The top-most low-index layer deposited on the first reflector layer is a half-wave optical thickness layer and serves as the first cavity layer. It is preferably deposited at the thickness desired for the longest wavelength of interest. The deposited cavity layer can then be patterned and etched at regions where shorter wavelengths of interest will be transmitted to the detector. For a two-color device, with two different color filter elements per device, such as the devices shown in FIGS. 7A-7D, this single lithography and etching step creates the desired arrangement of cavity filter elements with two different thicknesses within the first cavity layer. For devices designed to detect more than two colors, additional patterning and etching steps can be used to create the desired arrangements of cavity filter elements with the desired cavity thicknesses. Such fabrication steps are within the skill of the ordinary artisan.

A second reflector layer, corresponding to a coupling reflector layer, can then be added across the entire surface of the first cavity layer by deposition of additional alternating layers of high index and low index materials. As with the deposition of the first reflector layer, the final deposition of low index material can be made sufficiently thick so as to serve as the half-wave optical thickness for the longest wavelength of interest. The next cavity layer is completed by suitable patterning and etching to create arrangements of low-index cavities of the desired thicknesses at the desired locations on the device array. The above steps can be repeated to generate as many cavity layers and coupling reflector layers as is desired. The final cavity layer is typically capped by a top reflector layer, which can be any suitable material and is preferably a suitable layer of the high index material.

It should be understood that the above steps can be varied as desired to achieve the desired optical and physical properties of the different color filtration elements. While each element can be broadly described as a multi-cavity color filter, with the structure being built up from a bottom reflector through a series of cavities and coupling reflectors, and with the final cavity layer being capped with a top reflector, this general structure can subsequently be optimized for a specific response using simulations and optimization loops in software models. An exemplary design is provided in the Example section of the disclosure.

Thin-film interference filter elements, in particular multi-cavity interference filter elements, are ideally suited to the large-scale arrays of integrated analytical devices disclosed herein, where a limited number of different color filter elements, e.g., 2 different filter elements for distinguishing two colors in a sequencing reaction, are repeated in large arrays over the surface of a substrate. Such approaches are less suitable in devices where large numbers of different colors need to be distinguished from one another within a single unit cell, because the number of patterning and etching steps required is related to the number of different colors needing to be distinguished. See, for example, Wang et al. (2006) *Appl. Phys. B* 82:637 and U.S. Patent Application Publication Nos. 2008/0042782 and 2012/0327248 A1, which disclose bandpass filters requiring multiple masking and etching steps in order to obtain the necessary cavity thicknesses. Such complicated process requirements would generally preclude the use of multi-cavity interference filters in these devices.

Arrays of Integrated Analytical Devices

In order to obtain the volumes of sequence information that can be desired for the widespread application of genetic sequencing, e.g., in research and diagnostics, high throughput systems are desired. As noted above, and by way of example, in order to enhance the sequencing throughput of the system, multiple complexes are typically monitored, where each complex is sequencing a separate template sequence. In the case of genomic sequencing or sequencing of other large DNA components, these templates will typically comprise overlapping fragments of the genomic DNA. By sequencing each fragment, one can then assemble a contiguous sequence from the overlapping sequence data from the fragments.

As described above, and as shown in FIGS. 1A-1B, the template/DNA polymerase-primer complex of such a sequencing system is provided, typically immobilized, within an optically confined region, such as a zero mode waveguide (ZMW) or nanowell, or proximal to the surface of a transparent substrate, optical waveguide, or the like. Preferably, such reaction cells are arrayed in large numbers upon a substrate in order to achieve the scale necessary for genomic or other large-scale DNA sequencing approaches. Such arrays preferably comprise arrays of complete integrated analytical devices, such as, for example, the devices shown in the block diagrams of FIGS. 2 and 5. Examples of integrated systems comprising arrays of optical analytical devices are provided in U.S. Patent Application Publication Nos. 2012/0014837, 2012/0019828, 2012/0021525, and 2016/0061740, and in U.S. Pat. No. 9,372,308.

According to some aspects, the instant disclosure provides arrays of the integrated analytical devices described in detail above. Such arrays can be fabricated at ultra-high density, providing anywhere from 1000 nanoscale emission volumes per $cm^2$, to 1,000,000 nanoscale emission volumes per $cm^2$, or more. Thus, at any given time, it can be possible to analyze the reactions occurring in from 100, 1000, 3000, 5000, 10,000, 20,000, 50,000, 100,000, 1 Million, 5 Million, 10 Million, or even more nanoscale emission volumes or other reaction regions within a single analytical system or even on a single substrate.

Using the foregoing systems, simultaneous analysis of thousands, tens of thousands, hundreds of thousands, millions, or even tens of millions of nanoscale emission volumes in an array is possible. However, as the desire for multiplex increases, the density of nanoscale emission volumes on an array, and the ability to distinguish signals within such arrays, increases in difficulty, as issues of cross-talk (signals from neighboring nanoscale emission volumes contaminating each other as they exit the array), decreased signal:noise ratios arising from higher levels of denser illumination, and the like, increase. The arrays and methods of the instant disclosure address some of these issues by providing improved color filtration of optical signals passing through the integrated devices of the arrays.

Methods for Producing Arrays of Integrated Analytical Devices

In another aspect, the instant disclosure provides methods for producing arrays of integrated analytical devices. As described above, such arrays are useful, for example, in the large-scale sequencing of nucleic acids, including in particular, genomic sequencing. Such arrays can be produced by a variety of methods. One preferred approach for producing the instant arrays involves the use of microfabrication methods such as semiconductor or MEMS (micro electromechanical systems) processing methods, which have been highly developed for the production of integrated circuits. Similar processes have been used to create MEMS for a variety of applications including inkjet printers, accelerometers, pressure transducers, and displays (such as digital micromirror displays (DMDs)). Microfabrication methods can be applied to a large substrate such as a wafer, which can later be diced into many separate arrays, allowing for the production of many device arrays at one time.

The methods of the invention may, for example, apply resist processes, such as photoresists, to define structural elements on substrates or other layers. Etching processes can be used to produce three-dimensional structures, including component structures in the integrated analytical device. Deposition processes can be used to add layers onto the devices. Other semiconductor processes such as ashing, polishing, release, liftoff, and wet cleans can also be employed to create the structures of the invention, as described in more detail below.

For example, lithographic techniques can be used to define a mask layer out of polymeric materials, such as photoresists, using e.g., conventional photolithography, e-beam lithography, or the like. Alternatively, lithographic techniques can be applied in conjunction with layer deposition methods to deposit metal mask layers, e.g., using aluminum, gold, platinum, chrome, or other conventionally used metals, or other inorganic mask layers, e.g., silica based substrates such as silicon, $SiO_2$, or the like. Alternatively, negative tone processes can be employed to define pillars of resists that correspond to, for example, nanowells. See, e.g., U.S. Pat. No. 7,170,050, which is incorporated by reference herein in its entirety for all purposes. The mask layer can then be deposited over the resist pillars and the pillars can be subsequently removed. In particularly preferred aspects, both the underlying substrate and the mask layer are fabricated from the same material, which in particularly preferred aspects, is a transparent substrate material such as an $SiO_2$-based substrate such as glass, quartz, or fused silica. By providing the mask and underlying layers of the same material, one can ensure that the two layers have the same interactivity with the environments to which they are exposed, and thus minimize any hybrid surface interactions.

In the case of $SiO_2$-based substrates and mask layers, conventional fabrication processes can be employed. For example, a glass substrate bearing a surface-exposed feature, such as a waveguide, can have a layer of resist deposited over its surface. A negative of the mask layer is then defined by appropriate exposure and development of the resist layer to provide resist islands where one wishes to retain access to the underlying feature. The mask layer is then deposited over the surface and the remaining resist islands are removed, e.g., through a lift off process, to provide the openings to the underlying feature. In the case of metal layers, deposition can be accomplished through a number of means, including evaporation, sputtering or the like. Such processes are described in, e.g., U.S. Pat. No. 7,170,050. In the case of silica based mask layers, a chemical vapor deposition (CVD) process can be employed to deposit a silicon layer onto the surface. Following lift off of the resist layer, a thermal oxidation process can convert the mask layer to $SiO_2$. Alternatively, etching methods can be used to etch access points to underlying layers using conventional processes. For example, a silicon layer can be deposited over an underlying substrate. A resist layer is then deposited over the surface of the silicon layer and exposed and developed to define the pattern of the mask. The access points are then etched from the silicon layer using an appropriate differential etch to remove silicon but not the underlying $SiO_2$ substrate. Once the mask layer is defined, the silicon layer is again converted to $SiO_2$ using, e.g., a thermal oxidation process.

One aspect of the invention relates to a process for producing arrays of integrated analytical devices comprising the steps of: providing a substrate layer, which can be a light-sensitive detector layer, such as a CMOS sensor layer, a CCD layer, or the like; depositing a bottom reflector layer on the substrate layer, wherein the bottom reflector layer comprises alternating layers of a low refractive index material and a high refractive index material; depositing a first cavity layer on the bottom reflector layer, wherein the first cavity layer comprises the low refractive index material; patterning and etching the first cavity layer to create a first arrangement of first cavity filter elements having a first thickness and second cavity filter elements having a second thickness; depositing a first coupling reflector layer on the first cavity layer, wherein the first coupling reflector layer comprises alternating layers of the low refractive index material and the high refractive index material; depositing a second cavity layer on the first coupling reflector layer, wherein the second cavity layer comprises the low refractive index material; patterning and etching the second cavity layer to create a second arrangement of first cavity filter elements having the first thickness and second cavity filter elements having the second thickness; and depositing a top reflector layer on the array, wherein the top reflector layer comprises alternating layers of the low refractive index material and the high refractive index material. Unless specifically described, the order of the steps of the processes described herein can be altered, where suitable. In some embodiments, additional steps can be added, in particular the deposition and patterning of additional layers between the other layers of the array. A specific example of such a fabrication process is provided in detail below. Further examples of processes useful in the production of arrays of integrated analytical devices can be found in U.S. patent application Ser. No. 13/920,037.

In each of the above exemplary microfabrication techniques, the process begins with a clean substrate layer. The substrate layer used in the instant methods can be of any suitable rigid material. The substrate layer material can comprise, for example, an inorganic oxide material such as silica. A preferred substrate layer material comprises a detector layer, such as, for example, a CMOS wafer, i.e., a wafer made up of CMOS sensors or CCD arrays. See, for example, *CMOS Imagers From Phototransduction to Image Processing* (2004) Yadid-Pecht and Etienne-Cummings, eds.; Springer; *CMOS/CCD Sensors and Camera Systems* (2007) Holst and Lomheim; SPIE Press. In some cases, the substrate may already have some components of the devices fabricated on the surface. For example, in some methods, an array of thin-film laser rejection filters may have already been fabricated on the substrate prior to fabrication of the color filtration layer.

As mentioned above, the methods of the invention in some cases use resists for defining and producing structures with lithography. These resists can be, for example, photoresists or e-beam resists. The photoresists can be developed using UV, deep UV, G-line, H-line, Mine or other suitable wavelength or set of wavelengths. The type of resist that is used, and therefore the type of instrumentation that is employed for processing, will depend on the dimensions of the features that are created. Many resists are known in the art, and many are available commercially from companies such as Rohm and Haas and Shipley. The resists used in the processes of the invention can be negative or positive photoresists. Where a process is described herein using a negative photoresist, it is to be understood that a suitable positive photoresist can also be employed where practical, and vice versa. Where appropriate, chemical amplification can also be employed in order to increase the sensitivity of the resist. The removal of the resist, the cleaning, rinsing, ashing, and drying of the substrate can be performed as appropriate and as taught and known in the art.

Etching processes are used in some aspects of the invention in order to produce the three dimensional features in a substrate or in other layers, to fashion, for example, cavity filter elements, optical elements or lenses, and reaction volumes such as nanowells. The etching process that is used will depend on the type of material used, the dimensions of the features, and the resist system. In some cases wet etching or wet chemical etching is employed. Electrochemical etching can also be employed. In some embodiments plasma etching or reactive ion etching (RIE) is used as an etching process. Deep reactive ion etching (DRIE) can also be employed, for example, where structures having high aspect ratio are desired. Dry vapor phase etching, for example with xenon difluoride, can also be used. Bulk micromachining or surface micromachining can be used as appropriate to create the device structures of the disclosure. The etching used in the methods of the disclosure can be gray-scale etching. The conditions of the resist formation and etching are controlled to produce side walls having the desired geometries, such as having the desired side-wall angle.

Some processes of the invention involve the deposition of reflective layers, or cladding layers. The deposition of these reflective layers can be accomplished by wet processes including spinning on layers from solution, or by gas-phase processes. Suitable processes include electroplating, sputter deposition, physical vapor deposition, evaporation, molecular beam epitaxy, atomic layer deposition, and chemical vapor deposition. Metals can be used as the reflective layer and the cladding layer. Suitable metals include gold, nickel, aluminum, chromium, titanium, platinum, and silver. The reflective and/or cladding layers can comprise aluminum, which can be deposited by sputtering, for example using a commercially available sputter tool available from CVC, Novellus, or MRC.

Where layers are deposited during the processes of the invention, in some cases, the layers are treated before moving on to the next step in the process. For example, the deposited layer can be annealed, planarized, cleaned, passivated, or lightly etched in order to improve its properties.

In some methods of the invention, protective layers or sacrificial layers are deposited. The protective layers can be polymeric layers, or can be inorganic layers. Suitable protective or sacrificial layers include germanium (Ge) and amorphous silicon (a-Si). Protective layers can be used to produce features as described herein. The type of material for the protective or sacrificial layer can be chosen for its selective reactivity, for example to wet chemical etchants. For example, in some cases, the ability to selectively etch germanium with heated hydrogen peroxide in the presence of silicon dioxide and aluminum results in its being utilized to produce optical structures combined with nanowells.

In some processes, a pull-back process can be employed. A pull-back process generally involves etching in from the edges of a feature within a layer in order to reduce the dimensions of the feature. Pull-back can be performed using a wet chemical reagent that selectively reacts with a layer which has exposed edges. In some cases a germanium layer is pulled back using hydrogen peroxide.

Some methods employ a polishing step to remove a surface region from a surface. Suitable methods include chemical-mechanical polishing or chemical-mechanical planarization (CMP).

Some methods of the invention incorporate a planarization layer. The method for depositing the planarization layer depends on the type of material that is used. The planarization layer can be a hard material, such as an inorganic material, for example silicon nitride; it can be a metallic material such as aluminum; or it can be a soft material, such as a polymeric material, e.g. an organic or silicon based polymer. The planarization layer can be a glass, such as a silicon dioxide material. In some cases, the planarization layer comprises a spin-on glass such as a silicate, phosphosilicate or siloxane material. Suitable spin-on glass materials are available, for example, from Honeywell Corporation. The planarization layer can comprise, for example, a glass doped with other agents to control its melting properties, such a boro-phosphoro-silicate glass (BPSG). Suitable polymeric planarization materials include, for example, polyimides.

After the arrays of the instant disclosure are complete, such as by, for example, following the device design of the example below, the arrays can be further processed, such as, for example, by separating the arrays into individual chips and readying them for sequencing. The further processing steps will depend on the situation but can typically include the following treatments: surface treatment (a series of wet/vapor phase treatments to put down a specific surface that attracts the DNA polymerase enzyme to the bottom of the nanowell); stacking (a process to protect the top surface of the surface-treated device wafer and, in some cases, creating a well for the sequencing mixture); thinning (a process in which the composite top-plated and surface-treated device wafer can be thinned—including grinding lapping, polishing, or other treatments); dicing (a process in which the composite wafer is divided into individual chips using a standard semiconductor dicing saw); and packaging (a process involving a standard pick and place tool to mount the chips onto a substrate and create electrical/optical outputs for data collection). These further processing steps are either known in the art or are disclosed in references such as U.S. Patent Application Publication Nos. 2008/0176769 and 2011/0183409, which are incorporated by reference herein in their entireties for all purposes.

As just noted, the arrays of the invention can be incorporated into analysis systems for analyzing the multiple reactions occurring in the nanowells of the array. The arrays described herein typically have nanowells that are accessible to fluid from the top, and that are accessible for optical analysis from the bottom. The arrays are thus generally incorporated into a vessel into which a reaction mixture of interest is introduced. In some cases, the individual nanowells are all in contact with one volume of fluid, which can have, for example, multiple nucleic acid template molecules which can be analyzed, and which can have the nucleotides, cofactors, and other additives for carrying out the reaction to be analyzed.

The vessel that comprises the array can be placed within an instrument which has the appropriate optical components, computer controls, and data analysis systems. The vessel comprising the array can be held within the instrument such that the reaction conditions, such as the vessel temperature and vessel atmospheric conditions, can be controlled. The vessel atmospheric conditions can comprise the makeup of the gas above the sample, for example the humidity, and the level of other gaseous species such as oxygen.

It will be readily apparent to one of ordinary skill in the relevant arts that other suitable modifications and adaptations to the device arrays and methods described herein can be made without departing from the scope of the invention or any embodiment thereof.

Having now described the present invention in detail, the same will be more clearly understood by reference to the following Example, which is included herewith for purposes of illustration only and is not intended to be limiting of the invention.

Example

Figure 9:
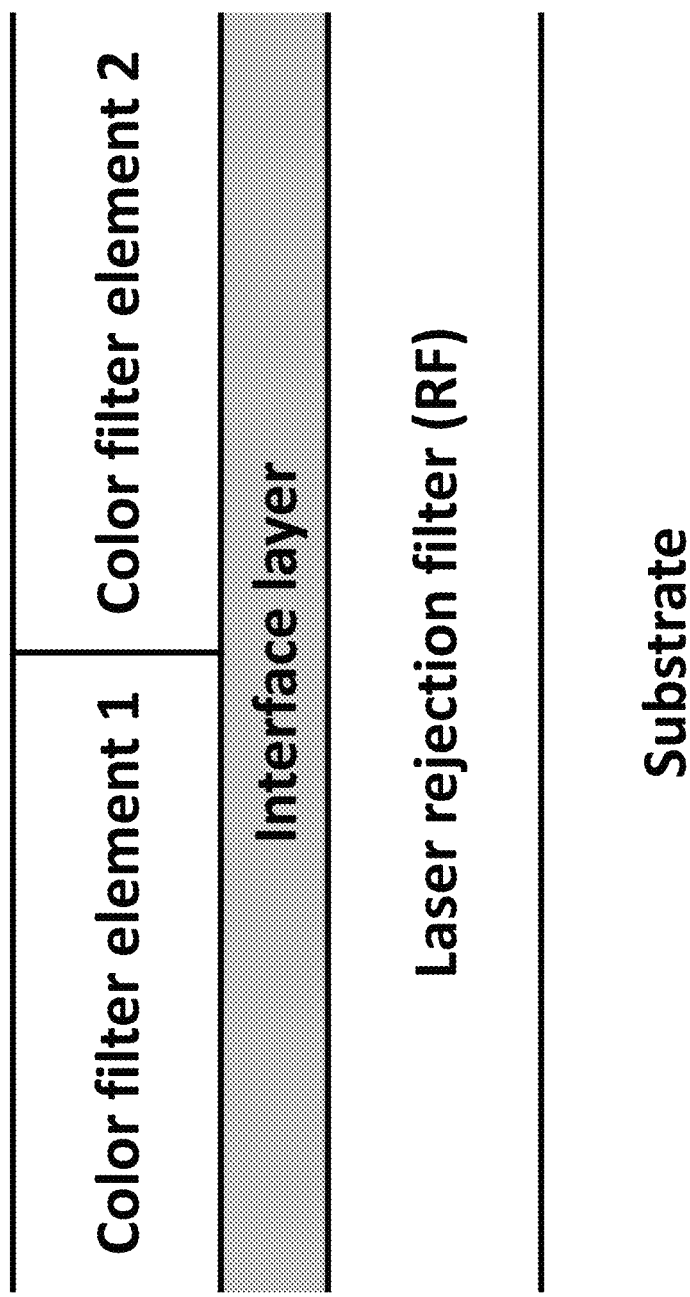
FIG. 9 shows an exemplary integrated analytical device of the disclosure.

A schematic of an exemplary device comprising a laser-rejection filter and a color filtration layer comprising two three-cavity dielectric filter elements, is provided in FIG. 9. In order to fabricate an array of such devices, a laser rejection filter (RF) layer comprising a number of pairs of low index/high index layers is first deposited on the substrate. A layer of low refractive index material is next deposited. This layer acts as an interface between the laser rejection filter (RF) layer and the color filtration layer.

Table 1 shows the structure of the two three-cavity filter stacks of the device of FIG. 9, which act as color filter element 1 and color filter element 2, respectively. Color filter element 1 is designed to pass 600 nm light, while color filter element 2 is designed to pass 660 nm light. These multi-cavity filters comprise an alternating stack of reflectors and transparent cavities.

The reflectors in the multi-cavity filters of this color filtration layer include alternating layers of two materials: a thin-film $SiO_2$ as the low index material and a thin-film silicon material as the high index material. The thicknesses of the layers in the reflectors are quarter-wave optical thicknesses.

In this example, the two color filter elements differ only in the thickness of their three low index cavity layers ($SiO_2$). To create the different cavities, a low refractive index layer is deposited first with a thickness equal to the thickest of the two required cavities. This layer is then patterned and etched to achieve the required thickness of the thinner cavity. The etching step creates the arrangement of first and second cavity filter elements, which are aligned with the pattern of first and second pixels on the detector layer.

TABLE 1

Design features for two three-cavity dielectric interference stacks used in a color filtration layer to pass optical signals at 600 nm and 660 nm. The layers in the stacks are listed in their order of fabrication, i.e., from the surface of the detector layer to the layer closest to the optical source. The layers identified as reflectors contain alternating layers of a thin-film silicon material and $SiO_2$ with quarter-wave optical thicknesses. The layers identified as cavities contain a single layer of $SiO_2$ with the indicated physical thicknesses.

|  | Thickness of layers in color filter element 1 | Thickness of layers in color filter element 2 |
|---|---|---|
| Reflector 1 | $\lambda/4$ | |
| Cavity 1 | 210 nm | 280 nm |
| Reflector 2 | $\lambda/4$ | |
| Cavity 2 | 210 nm | 280 nm |
| Reflector 3 | $\lambda/4$ | |
| Cavity 3 | 210 nm | 280 nm |
| Reflector 4 | $\lambda/4$ | |

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An array of integrated analytical devices comprising:
an array of nanoscale emission volumes; and
an array of first and second multi-cavity filter elements, each first and second multi-cavity filter element optically coupled to a nanoscale emission volume;
wherein each multi-cavity filter element comprises
a bottom reflector layer comprising alternating layers of a first color filter element material and a second color filter element material, wherein the second color filter element material has a higher refractive index than the first color filter element material;
a first cavity layer disposed on the bottom reflector layer, wherein the first cavity layer comprises the first color filter element material;
a first coupling reflector layer disposed on the first cavity layer, wherein the first coupling reflector layer comprises alternating layers of the first color filter element material and the second color filter element material;
a second cavity layer disposed on the first coupling reflector layer, wherein the second cavity layer comprises the first color filter element material; and
a top reflector layer disposed above the second cavity layer, wherein the top reflector layer comprises alternating layers of the first color filter element material and the second color filter element material;
wherein the first and second cavity layers of the first multi-cavity filter element have a first thickness and the first and second cavity layers of the second multi-cavity filter element have a second thickness.

2. The array of claim 1, wherein the second color filter element material comprises silicon.

3. The array of claim 2, wherein the second color filter element material is a thin-film silicon material.

4. The array of claim 1, wherein the second color filter element material has a refractive index from 2.5 to 5.0.

5. The array of claim 1, wherein the first color filter element material comprises a silicon oxide.

6. The array of claim 5, wherein the first color filter element material is a thin-film silicon dioxide material.

7. The array of claim 1, wherein the first color filter element material has a refractive index from 1.0 to 1.8.

8. The array of claim 1, wherein each first and second multi-cavity filter element independently comprises 2 to 6 cavity layers.

9. The array of claim 1, wherein each first and second multi-cavity filter element independently comprises 3 to 7 reflector layers.

10. The array of claim 1, wherein the first thickness of the cavity layers of the first multi-cavity filter element is a first half-wave optical thickness or multiple thereof, and the second thickness of the cavity layers of the second multi-cavity filter element is a second half-wave optical thickness or multiple thereof.

11. The array of claim 10, wherein the first and the second thicknesses are in a range from 150 to 350 nm.

12. The array of claim 1, wherein the reflector layers of the first multi-cavity filter element and of the second multi-cavity filter element are the same.

13. The array of claim 1, wherein the filter elements transmit visible light and the reflector layers comprise alternating layers of a quarter-wave optical thickness.

14. The array of claim 1, further comprising an array of detector elements, each detector element comprising a first pixel and a second pixel, wherein the multi-cavity filter elements are optically coupled to the detector elements.

15. The array of claim 14, further comprising an array of lens elements disposed between the array of nanoscale emission volumes and the array of detector elements.

16. The array of claim 15, wherein each lens element comprises a diffractive beam shaping element, wherein the nanoscale emission volumes are optically coupled through the beam shaping elements and the first multi-cavity filter elements to the first pixels and are optically coupled through the beam shaping elements and the second multi-cavity filter elements to the second pixels.

17. The array of claim 14, further comprising an excitation source optically coupled to the nanoscale emission volumes.

18. The array of claim 17, wherein the excitation source is a waveguide excitation source.

19. The array of claim 17, further comprising a laser rejection filter element disposed between the excitation source and the array of detector elements.

20. The array of claim 19, wherein the laser rejection filter element is disposed between the array of multi-cavity filter elements and the detector layer.

21. The array of claim 19, wherein the laser rejection filter element is a thin-film interference filter.

22. The array of claim 21, wherein the thin-film interference filter comprises alternating layers of a first laser rejection filter material and a second laser rejection filter material, wherein the second laser rejection filter material has a higher refractive index than the first laser rejection filter material.

23. The array of claim 22, wherein the second laser rejection filter material comprises silicon.

24. The array of claim 23, wherein the second laser rejection filter material is a thin-film silicon material.

25. The array of claim 22, wherein the second laser rejection filter material has a refractive index from 2.5 to 5.0.

26. The array of claim 22, wherein the first laser rejection filter material comprises a silicon oxide.

27. The array of claim 26, wherein the first laser rejection filter material is a thin-film silicon dioxide material.

28. The array of claim 22, wherein the first laser rejection filter has a refractive index from 1.0 to 1.8.

* * * * *